United States Patent [19]

Geimer

[11] Patent Number: 5,232,687
[45] Date of Patent: Aug. 3, 1993

[54] FLUID DISPENSER FOR GERM-FREE FLUID

[75] Inventor: Gunter Geimer, Schonenberg-Kubelberg, Fed. Rep. of Germany

[73] Assignee: URSAPHARM Arzneimittel GmbH, Bubingen, Fed. Rep. of Germany

[21] Appl. No.: 739,918

[22] Filed: Aug. 2, 1991

[30] Foreign Application Priority Data

Aug. 29, 1990 [DE] Fed. Rep. of Germany ....... 4027320

[51] Int. Cl.⁵ .............................................. A61M 1/00
[52] U.S. Cl. ..................... 424/45; 424/400; 424/405
[58] Field of Search ................ 424/405, 618, 619, 45; 128/DIG. 1, DIG. 7, DIG. 10, DIG. 13, 474, 912, 917, 655; 604/33, 38, 123, 207

[56] References Cited

U.S. PATENT DOCUMENTS

| | | | |
|---|---|---|---|
| 4,685,596 | 8/1987 | Mattheis | 222/389 |
| 5,034,000 | 7/1991 | Freitas et al. | 604/30 |
| 5,080,648 | 1/1992 | D'Antonio | 604/72 |

FOREIGN PATENT DOCUMENTS 190504A 8/1986 European Pat. Off. ............ 424/618

OTHER PUBLICATIONS

Pharmazeutische Zeitung, 124 No. 20, May 17, 1979, pp. 946-957.

Primary Examiner—Thurman K. Page
Assistant Examiner—N. Levy
Attorney, Agent, or Firm—Scully, Scott, Murphy & Presser

[57] ABSTRACT

A fluid dispenser incorporating an oligodynamically germicidally active substance for maintaining the dispensation of germ-free fluid, particularly eye drops. The delivery passage from a supply container associated with the fluid dispenser of the invention contains an oligodynamically germicidally active substance that is soluble in the fluid to be dispensed. The device does not require air pressure within the container, thus eliminating one avenue for the introduction of germs into the fluid. The device includes a metering pump and inlet and outlet valves. The above-mentioned fluid soluble oligodynamically germicidally active substance is situated in the region of the inlet valve or the inlet thereto and/or the outlet therefrom.

16 Claims, 1 Drawing Sheet

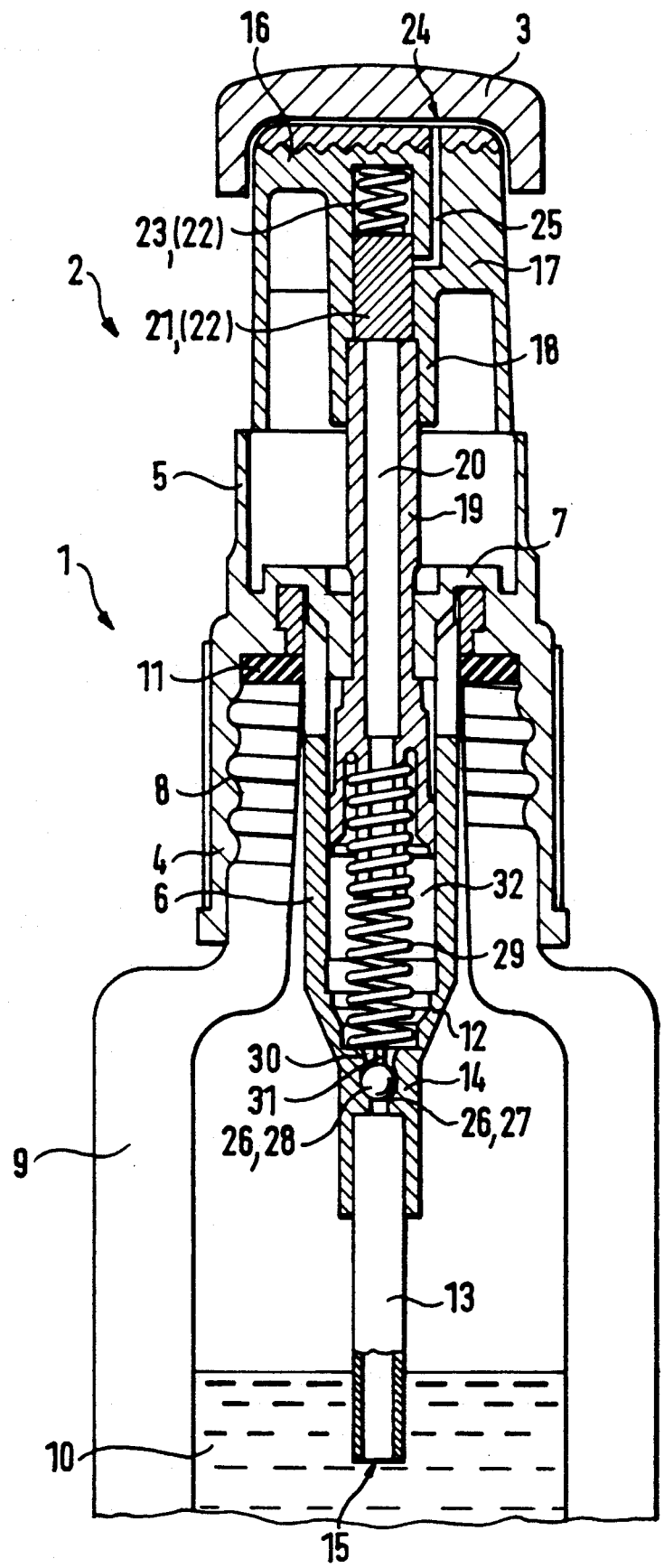

FLUID DISPENSER FOR GERM-FREE FLUID

TECHNICAL FIELD OF THE INVENTION

The invention relates to a fluid dispenser for germfree fluid.

BACKGROUND OF THE INVENTION AND PRIOR ART

In the Pharmazeutische Zeitung, 124, No. 20, of 17th May 1979, on pages 949 and 950, a fluid dispenser is described that has the form of a dropping pipette and is attached to a container containing eye-drops. Inside the dropping pipette a silver deposit consisting of a layer of silver or a difficultly-soluble silver salt is disposed so that airborne germs drawn in with the drops that run back into the container have to pass an antimicrobially (oligodynamically) active silver layer before they enter the container. It is also stated that ceramic rings with silver chloride embedded therein and having a diameter of 9 mm have been found to be suitable. These ceramic rings can be firmly installed in the droppers of all the usual kinds of pharmacists, eye-dropper bottles simply by pushing them in. This method of introducing the silver deposit into the droppers has the disadvantage that only the drops running back along the walls of the dropper come into contact with the silver deposit, but not the portions of the liquid in the interior of the column of fluid which flows back into the container from the dropper after use in the usual way with the dropper facing downwards. Each use of the eye-drop container thus leads to contamination of the eye-drops. A further disadvantage is that the interior of the container is in contact with the ambient air through the dropper, so that even while it is not being used germs constantly find their way in and lead to contamination of the eye-drops in the container.

OBJECT OF THE INVENTION

It is an object of the invention to improve a fluid dispenser of the kind referred to above so that contamination of the germ-free fluid is reliably prevented.

SUMMARY OF THE INVENTION

It will be understood that all references hereinafter to oligodynamic activity and to oligodynamically active substances are to oligodynamic germicidal activity and to oligodynamically germicidally active substances respectively.

The flow cross-section of the inlet valve is so small that the fluid flowing through it comes completely into contact with the oligodynamically germicidally active substance, so that even with short contact times the whole of the germs present in the fluid are killed. A comparable effect is achieved if the oligodynamically active substance is disposed in the correspondingly narrow inlet or outlet passages of the inlet valve. Germs present in the residual liquid that remains in the inlet valve, particularly when a piston valve is used as the inlet valve and a fluid of relatively high viscosity is used, and forms a connection between the ambient air and the fluid supply, are also reliably and completely destroyed. Here a particularly intensive germicidal action results from the more prolonged contact between the liquid and the oligodynamically active substance. The metering pump operates without air pressure compensation, so that contamination of the fluid supply through the air that flows into the container to effect the pressure compensation in the operation of conventional metering pumps is prevented. The fluid dispenser of the invention ensures that the fluid in the supply container is kept germ-free, so that it is not necessary either to add preservatives or to introduce the oligodynamically active substance into the container.

Particularly when a seat valve is used as the inlet valve, the particularly intensive germicidal action due to prolonged contact of the fluid with the oligodynamically active substance can be obtained by keeping the through passage, at least in the neighborhood of the inlet valve, constantly full of the fluid.

To assist in maintaining freedom from germs the oligodynamically active substance is preferably located in an outlet valve that can close the delivery opening, and/or in the associated inlet or outlet passages. Germs can be prevented from penetrating into this outlet valve by covering the delivery opening with a cap having the oligodynamically active substance inside it.

Advantageously the oligodynamically active substance is situated on the closure member of the inlet and/or outlet valve, or forms at last part thereof.

Alternatively or in addition the oligodynamically active substance may be on the valve seat or valve housing that cooperates with the closure member of the inlet and/or outlet valve, or form at least part thereof.

Another possibility is to provide the oligodynamically active substance on a spring that acts on the closure member of the inlet valve and/or the outlet valve. Furthermore the oligodynamically active substance may be provided on at least part of the rising tube forming the inlet passage to the inlet valve, or form at least part thereof.

Another useful construction is one in which the oligodynamically active substance is located in the region between the two valves on at least part of the through passage, or forms at least part thereof.

The oligodynamically active substance may be embedded in a carrier material, preferably corundum.

It is preferred to employ silver or an alloy thereof in metallic form or in the form of a compound, for example as a salt, as the oligodynamically active substance.

Silver exhibits the most favourable therapeutical index in terms of concentration in parts per billion. Other heavy metals, for example cadmium, copper, brass or the like, can however be used.

BRIEF DESCRIPTION OF THE DRAWINGS

The invention will now be described in more detail, by way of example, with reference to the single Figure of the drawings, which shows in longitudinal section an embodiment of the invention.

DETAILED DESCRIPTION OF A PREFERRED EMBODIMENT OF THE INVENTION

As shown in the Figure, the device comprises a metering pump consisting of a cylindrical pump body 1, an operating plunger 2 and a cap 3.

The pump body 1 comprises a first hollow cylindrical body part 4, shown in the drawing as open at the bottom, a second hollow cylindrical body part 5 of smaller diameter, open at the top in the drawing, and a hollow cylinder 6 that is open at both ends and is fixed centrally on an inwardly directed annular flange 7 in the transition region between the two parts 4,5 of the pump body. The first body part 4 has an internal screw thread 8 into which a container 9 filled with a germ-free fluid, in the present case eye-drops, and indicated only generally, can be screwed. A seal 11 is provided on the underside (in the drawing) of the annular flange 7 to ensure an air-tight seal between the container 9 and the pump body 4. In the neighborhood of the outlet from the first body part 4 of the pump the hollow cylinder 6 has a conically tapered-down transition part 12 that connects with a cylindrical valve section 14 of smaller diameter leading to a rising tube 13. The open bottom end of the rising tube 13 forms the inlet opening 15 of the metering pump.

The operating plunger 2 comprises an outer hollow cylindrical part 17, shown in the drawing as open at the bottom and closed at the top by a head 16, and a hollow inner cylindrical part 18 extending centrally downwards from the head 16. The diameter of the hollow outer cylindrical part 17 is smaller than that of the first pump body part 4.

A piston 19 that fits inside the hollow cylinder 6 and has a through bore 20 is fixed at its top end in the inner hollow cylinder part 18. A piston valve 21 of an outlet valve 22 that fits inside the hollow cylindrical part 18 is supported between the end part of the piston 19 at one end and at the other end on the head 16 via a spring 23. An outlet passage 25 leading to a delivery opening 24 on the head 16 is connected to the interior of the inner hollow cylindrical part 18 at the level of the piston valve 21.

An inlet valve 26 comprising a ball 28 cooperating with a valve seat 27 is formed in the valve part 14. A spring 29 fixed to the piston 19 is supported on a projection 30 on the valve part 14 and acts on the ball 28 via a pin 31. The space inside the hollow cylinder 6 between the piston 19 and the valve part 14 is indicated by the reference numeral 32.

The valve ball 28 and the piston valve 21 consist of corundum having embedded therein an oligodynamically active substance, which in the present case is silver. In addition the valve seat 27 and the inner side of the inner hollow cylinder part 18 in the region of the piston valve 21 may be coated with silver. The spring(s) 23 and/or 29 may also be coated with silver. Likewise the lower end part of the rising tube 13 and/or part of the wall of the through bore 20 may be coated with silver. In addition the inner side of the cap 3 facing the delivery opening 24 is also coated with silver. Although in the present example the silver is used in the form of metallic silver, it is also possible to use a silver salt, for example a silver halide, or another heavy metal. The oligodynamic activity of heavy metals, especially silver, is known and does not need to be explained in more detail here. It need only be said that the silver dissolves in water in concentrations of some parts per billion. The silver ions thus liberated have a bacteriostatic and bactericidal action on the germs that may penetrate and thus destroy them.

The metering pump of the invention operates without air pressure compensation, that is to say, no pressure compensation takes place in the container 9 through the inflow of air during its operation.

The metering pump of the invention operates as follows: when the user removes the cap 3 and depresses the operating plunger 2 so as to push it into the second pump body part 5 a corresponding movement of the piston 19 against the force of the spring 29 simultaneously takes place. This presses the ball 28 harder against the valve seat 27 and applies pressure to the liquid 10 that has been sucked into the inner space 32 and the through bore 20 during the previous operation of the metering pump. This pressure displaces the piston valve 21 of the outlet valve 22 against the force of the spring 23, so that the connection to the outlet passage 25 is opened and a precisely measured quantity of the liquid 10 is delivered through the delivery opening 24. As soon as the piston 19 reaches its dead centre position, the pressure in the inner space 32 and in the through bore 20 drops so far that the outlet valve 22 closes and the inlet valve 26 opens, so that liquid 10 is sucked out of the container 9. The inlet valve 26 then closes again. Thereupon the user replaces the cap 3 on the plunger 2 and thereby closes the delivery opening 24.

Liquid remaining at the delivery opening 24, in the outlet valve 22, and possibly in the through bore 20, as well as in the inner space 32 and in the inlet valve 29, come into contact with the respective silver deposits, so that the germs they contain are killed by the silver ions that are released. Silver ions are also released from the bottom part of the rising tube 13 into the liquid 10 in the container 9.

What is claimed is:

1. A fluid dispenser for germ-free fluid, comprising a through passage connecting an inlet opening for fluid contained in a supply container and a delivery opening for said fluid and having therein an oligodynamically germicidally active substance that is soluble in the fluid, said device comprising a metering pump operating without air pressure compensation and having an inlet valve for closing said inlet opening and having said fluid-soluble oligodynamically germicidally active substance embedded in a carrier material contained in at least one of said inlet valve and its associated inlet and outlet passages; an outlet valve for closing said delivery opening, wherein said oligodynamically germicidally active substance is embedded in a carrier material contained in at least one of said outlet valve and its associated inlet and outlet passages; said outlet valve including a closure member which contains a carrier material having said oligodynamically germicidally active substance embedded therein; and at least one spring means acting on the closure member of the outlet valve, said at least one spring means having said oligodynamically germicidally active substance embedded in a carrier material on at least on a surface thereof.

2. A fluid dispenser according to claim 1, wherein said through passage is constantly filled, at least in the region of said inlet valve, with said fluid.

3. A fluid dispenser according to claim 1, wherein said oligodynamically germicidally active substance is situated on the inner side of a cap that can be fitted on to said fluid dispenser to cover said delivery opening.

4. A fluid dispenser according to claim 1, wherein said inlet valve includes a closure member which contains said oligodynamically germicidally active substance.

5. A fluid dispenser according to claim 4, wherein said inlet valve further includes a valve seat cooperating with the closure member wherein said valve seat contains said oligodynamically germicidally active substance.

6. A fluid dispenser according to claim 1, wherein said outlet valve further includes a valve seat cooperating with the closure member wherein said valve seat contains said oligodynamically germicidally active substance.

7. A fluid dispenser according to claim 1, wherein said inlet valve is a piston valve and a valve housing cooperating with a closure member of said inlet valve, said valve housing containing said oligodynamically germicidally active substance.

8. A fluid dispenser according to claim 1, wherein said outlet valve is a piston valve and a valve housing cooperating with a closure member of said outlet valve, said valve housing containing said oligodynamically germicidally active substance.

9. A fluid dispenser according to claim 4 which includes at least on spring acting one the closure member of the inlet valve said at least one spring having said oligodynamically germicidally active substance situated at least on a surface thereof.

10. A fluid dispenser according to claim 2, wherein at least a surface of at least part of a rising tube forming an inlet passage to said inlet valve contains said oligodynamically germicidally active substance.

11. A fluid dispenser according to claim 1, wherein at least a surface of at least part of said through passage in the region between said inlet and outlet valves contains said oligodynamically germicidally active substance.

12. A fluid dispenser according to claim 1, wherein said carrier material is corundum.

13. A fluid dispenser according to claim 1, wherein said oligodynamically germicidally active substance is selected from the group consisting of heavy metals and alloys thereof.

14. A fluid dispenser according to claim 13, wherein said oligodynamically germicidally active substance is selected from the group consisting of heavy metals and alloys thereof in metallic form.

15. A fluid dispenser according to claim 13, wherein said oligodynamically germicidally active substance is selected from the group consisting of heavy metals and alloys thereof in the form of a compound such as a salt.

16. A fluid dispenser according to claim 13, wherein said oligodynamically germicidally active substance is selected from the group consisting of silver, silver salts and other silver compounds.

* * * * *